United States Patent [19]

Sanchez

[11] Patent Number: 4,916,141

[45] Date of Patent: Apr. 10, 1990

[54] (S)-7-(3-AMINO-1-PYRROLIDINYL)-1-CYCLOPROPYL-6-FLUORO-1,4-DIHYDRO-4-OXO-1,8-NAPHTHYRIDINE-3-CARBOXYLIC ACID

[75] Inventor: Joseph P. Sanchez, Novi, Mich.

[73] Assignee: Warner-Lambert Company, Morris Plains, N.J.

[21] Appl. No.: 329,461

[22] Filed: Mar. 28, 1989

[51] Int. Cl.$^4$ .................... C07D 471/04; A61K 31/44
[52] U.S. Cl. ...................................... 514/300; 546/123
[58] Field of Search ..................... 546/123; 514/300

[56] References Cited

U.S. PATENT DOCUMENTS 4,649,144 3/1987 Matsumoto et al. ................. 546/123

Primary Examiner—Mary C. Lee
Assistant Examiner—Bernard I. Dentz
Attorney, Agent, or Firm—Ronald A. Daignault

[57] ABSTRACT

The novel (S)-7-(3-amino-1-pyrrolidinyl)-1-cyclopropyl-6-fluoro-1,4-dihydro-4-oxo-1,8-n phthyridine-3-carboxylic acid, lower alkyl esters and pharmaceutically acceptable salts thereof are described as well as a method for its manufacture, formulation, and use in treating bacterial infections.

4 Claims, No Drawings

(S)-7-(3-AMINO-1-PYRROLIDINYL)-1-CYCLOPROPYL-6-FLUORO-1,4-DIHYDRO-4-OXO-1,8-NAPHTHYRIDINE-3-CARBOXYLIC ACID

BACKGROUND OF THE INVENTION

U.S. Pat. No. 4,649,144 discloses 7-(3-amino-1-pyrrolidinyl)-1-Cyclopropyl-6-fluoro-1,4-dihydro-4-oxo-1,8-naphthyridine-3-carboxylic acid as having antibacterial activity. In the patent, it is recognized that there is an asymmetric carbon atom on the pyrrolidine ring of the compound and that the compound can exist in optically active forms. Nevertheless, the patent does not describe the synthesis of these optically active forms nor does it describe or suggest which, if any, of the optically active forms would have antibacterial activity equal, better or less than the racemic compound, the compound specifically described in the patent.

We have now found that the S form of 7-(3-amino-1-pyrrolidinyl)-1-cyclopropyl-6-fluoro-1,4-dihydro-4-oxo-1,8-naphthyridine-3-carboxylic acid has significantly better activity against both gram-positive and gram-negative bacteria in vitro as well as in vivo. The S isomer is surprisingly not only better than its opposite R isomer but also better than the racemic compound described in the above patent.

SUMMARY OF THE INVENTION

Accordingly, the present invention is directed to the S optical isomer of 7-(3-amino-1-pyrrolidinyl)-1-cyclopropyl-6-fluoro-1,4-dihydro-4-oxo-1,8-naphthyridine-3-carboxylic acid, its lower alkyl esters or a pharmaceutically acceptable acid addition or base salt thereof.

The present invention also concerns a pharmaceutical composition containing the above compound together with a pharmaceutical excipient in a dosage form for treating bacterial infections.

Finally, the present invention is directed to a method of treating bacterial infections in mammals by administering to said mammal in need thereof an antibacterially effective amount of the above compound in unit dosage form.

DETAILED DESCRIPTION

Compounds of the present invention may be readily prepared by treating a 7-halo-1-cyclopropyl-6-fluoro-1,4-dihydro-4-oxo-1,8-naphthyridine-3-carboxylic acid or a lower alkyl ester wherein lower alkyl is one to four carbon atoms, with an (S)-3-[[lower alkyloxycarbonyl]amino]pyrrolidine in the presence of base and optionally in the presence of an organic solvent at approximately ambient to somewhat elevated temperatures, e.g., 25°–100° C.

Other blocking groups, in addition to lower alkyloxycarbonyl groups, can be formyl, acetyl, trifluoroacetyl; $\beta,\beta,\beta$-trichloroethoxycarbonyl, $\beta$-iodoethoxycarbonyl; aryloxycarbonyl group such as benzyloxycarbonyl, p-methoxybenzyloxycarbonyl, phenoxycarbonyl; silyl groups such as trimethylsilyl; and groups such as trityl, tetrahydropyranyl, vinyloxycarbonyl, o-nitrophenyl, sulfenyl, diphenylphosphinyl, p-toluenesulfonyl, and benzyl. As stated above, the groups may be removed by acid hydrolysis but also can be removed by base hydrolysis, and the trityl group, for example, may be removed by hydrogenolysis.

In addition to ambient temperatures, the reaction between the protected aminopyrrolidine and the haloquinoline can be carried out in a range of from 20° C. to about 150° C.; higher temperatures usually require shorter reaction times and may be prepared from known starting materials by standard procedures or by variations thereof.

For example, 7-chloro-1-cyclopropyl-6-fluoro-1,4-dihydro-4-oxo-1,8-naphthyridine-3-carboxylic acid may be prepared by a series of reactions starting from 4-(6-chloro-3-nitro-2-pyridinyl)-1-piperazinecarboxylic acid, ethyl ester. The intermediate, 1-cyclopropyl-6-fluoro-1,4-dihydro-4-oxo-7-(1-piperazinyl)-1,8-naphthyridine-3-carboxylic acid can be converted to the 7-hydroxy derivative with a mixture of nitric and sulfuric acids which is then replaced by chlorine by treatment with phosphorus oxychloride to give the desired intermediate. The synthesis of both of the above N-cyclopropyl intermediates is described in the Preparative Examples.

The (S)-protected aminopyrrolidine may be prepared in accordance with the procedures described in the examples herein.

The compounds of the invention are capable of forming both pharmaceutically acceptable acid addition and/or base salts. Base salts are formed with metals or amines, such as alkali and alkaline earth metals or organic amines. Examples of metals used as cations are sodium, potassium, magnesium, calcium, and the like. Also included are heavy metal salts such as for example silver, zinc, cobalt, and cerium. Such heavy metal salts are effective in the treatment of burns especially when applied to the affected surface of a burn victim either directly or in combination with a physiologically acceptable carrier such as a water dispersible, hydrophilic carrier. Examples of suitable amines are N,N'dibenzylethylenediamine, chloroprocaine, choline, diethanolamine, ethylenediamine, N-methylglucamine, and procaine.

Pharmaceutically acceptable acid addition salts are formed with organic and inorganic acids.

Examples of suitable acids for salt formation are hydrochloric, sulfuric, phosphoric, acetic, citric, oxalic, malonic, salicylic, malic, gluconic, fumaric, succinic, ascorbic, maleic, methanesulfonic, and the like. The salts are prepared by contacting the free base form with a sufficient amount of the desired acid to produce either a mono or di, etc salt in the conventional manner. The free base forms may be regenerated by treating the salt form with a base. For example, dilute solutions of aqueous base may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention. Use of excess base gives the corresponding basic salt.

The compounds of the invention can exist in unsolvated as well as solvated forms, including hydrated forms. In general, the solvated forms, including hydrated forms and the like are equivalent to the unsolvated forms for purposes of the invention.

The alkyl groups contemplated by the invention comprise both straight and branched carbon chains of from one to about three carbon atoms except when specifically stated to be greater than three carbon atoms. Representative of such groups are methyl, ethyl, propyl, isopropyl, and the like.

The alkoxy groups contemplated by the invention comprise both straight and branched carbon chains of from one to about six carbon atoms unless otherwise specified. Representative of such groups are methoxy, ethoxy, propoxy, i-propoxy, t-butoxy, hexoxy, and the like.

The term halogen or halo is intended to include fluorine, chlorine, bromine, and iodine unless otherwise specified.

The compounds of the invention can be prepared and administered in a wide variety of oral, parenteral and topical dosage forms. It will be obvious to those skilled in the art that the following dosage forms may comprise as the active component, a compound of the present invention or a corresponding pharmaceutically acceptable salt thereof.

For preparing pharmaceutical compositions from the compounds described by this invention, inert, pharmaceutically acceptable carriers can be either solid or liquid. Solid form preparations include powders, tablets, dispersible granules, capsules, cachets, suppositories, and ointments. A solid carrier can be one or more substances which may also act as diluents, flavoring agents, solubilizers, lubricants, suspending agents, binders, or tablets disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions, suspensions and emulsions. As an example may be mentioned water or water-propylene glycol solutions for parenteral injection. Such solutions are prepared so as to be acceptable to biological systems (isotonicity, pH, etc). Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspension suitable for oral use can be made by dispersing the finely divided active component in water with viscous material, i.e., natural or synthetic gums, resins, methyl cellulose, sodium carboxymethyl cellulose, and other well-known suspending agents.

Ointment preparations contain heavy metal salts of a compound of Formula I with a physiologically acceptable carrier. The carrier is desirably a conventional water-dispersible hydrophilic or oil-in-water carrier, particularly a conventional semi-soft or cream-like water-dispersible or water soluble, oil-in-water emulsion which may be applied to an affected burn surface or infected surface with a minimum of discomfort. Suitable compositions may be prepared by merely incorporating or homogeneously admixing finely divided compounds with the hydrophilic carrier or base or ointment.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, powders in vials or ampoules, and ointments in tubes or jars. The unit dosage form can also be a capsule, cachet, tablet, gel or cream itself or il can be the appropriate number of any of these packaged forms.

The quantity of active compound in a unit dose of preparation may be varied or adjusted from 1 mg to 100 mg according to the particular application and the potency of the active ingredient.

In therapeutic use as agents for treating bacterial infections the compounds utilized in the pharmaceutical method of this invention are administered at the initial dosage of about 3 mg to about 40 mg per kilogram daily. A daily dose range of about 6 mg to about 14 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The compounds of the invention display antibacterial activity when tested by the microtitration dilution method as described in Heifetz, et al, Antimicr. Agents and Chemot. 6, 124 (1974), which is incorporated herein by reference. By the use of the above reference method, the following minimum inhibitory concentration values (MICs in $\mu$g/ml) were obtained for the compound of the present invention, (S)-7-(3-amino-1-pyrrolidinyl)-1-cyclopropyl-6-fluoro-1,4-dihydro-4-oxo-1,8-naphthyridine-3-carboxylic acid, the corresponding (R) isomer and the racemic compound as described in U.S. Pat. No. 4,649,144.

In addition to the MIC data in the following table for the above compounds, there is also provided in vivo data.

The in vivo experiments on the bacteria named are expressed in terms of median protective doses ($PD_{50}$) on the test animals to which the compounds were administered orally and subcutaneously. The measurement of PDso was carried out according to the following procedure:

Therapeutic activities of the compounds were compared in acute mouse protection tests in which 18–22 g female Charles River CD-1 mice were used. Oral and subcutaneous doses in twofold rising incremental series were administered concurrently with bacterial challenge. Challenges were accomplished by the intraperitoneal injection of an estimated 100 median lethal doses in 0.5 ml volumes of 5% hog gastric mucin or tryptic soy broth. Generally, greater than 90% of the untreated controls died within 48–72 hours. Final survival percentages, obtained after 4–7 days of observation among groups of 8–16 mice, were used to estimate median protective doses ($PD_{50}$) by the log-probit method.

| Organisms | "S" Isomer | | | "R" Isomer | | | Racemic | | |
|---|---|---|---|---|---|---|---|---|---|
| | MIC | PD$_{50}$ P.O. | PD$_{50}$ S.C. | MIC | PD$_{50}$ P.O. | PD$_{50}$ S.C. | MIC | PD$_{50}$ P.O. | PD$_{50}$ S.C. |
| *Enterobacter cloacae* MA 2646 | 0.013 | | | 0.025 | | | 0.025 | | |
| *Escherichia coli* Vogel | 0.006 | 0.7 | 0.35 | 0.013 | 0.51 | 0.35 | 0.013 | 2.0 | 0.6 |
| *Klebsiella pneumoniae* MGH-2 | 0.013 | | | 0.025 | | | 0.025 | | |
| *Proteus rettgeri* M 1771 | 0.025 | | | 0.05 | | | 0.1 | | |
| *Pseudomonas aeruginosa* UI-18 | 0.1 | 3.5 | 2.1 | 0.4 | | | 0.05 | 7.3 | 3.2 |
| *Staphylococcus aureus* H 228 | 0.05 | | | 0.2 | | | 0.2 | | |
| *Staphylococcus aureus* UC-76 | 0.013 | | | 0.05 | | | 0.013 | | |
| *Staphylococcus faecalis* MGH-2 | 0.1 | 19 | 14 | 0.2 | 45 | 34 | 0.2 | 58 | 33 |
| *Streptococcus pneumoniae* SV-1 | 0.05 | 19 | 9 | 0.1 | | | 0.2 | 32 | 14 |
| *Streptococcus pyogenes* C-203 | 0.05 | | | 0.2 | | | 0.2 | | |

The following examples are illustrative of the present invention.

PREPARATION OF THE (S) AND (R) 3-PROTECTED AMINOPYRROLIDINES

(S)-3-Hydroxypyrrolidine

A solution of 22.5 g (105 mmol) of 1-benzyl-3(S)-pyrrolidinol (J. Am. Chem. Soc., 1986, 108, 2049) hydrochloride in 400 ml of methanol was treated with 2.0 g of 20% palladium on carbon and shaken in an atmosphere of hydrogen at temperatures of 23°–26.5° C. and pressures of 48.4–51.2 psi for 21 hours. The catalyst was removed by filtration through Celite and the solvent was removed in vacuo to give 12.9 g of the title compound as a light yellow oil.

(R)-3-Hydroxypyrrolidine

The above procedure was followed using 30.4 g (142 mmol) of 1-benzyl-3(R)-pyrrolidinol (J. Am. Chem. Soc., 1986, 108, 2049) hydrochloride, 600 ml of methanol, and 3.0 g of 20% palladium on carbon to give 14.8 g of the title compound as a light yellow oil.

(R)-3-Hydroxy-1-pyrrolidinecarboxylic acid, phenylmethyl ester

A solution of 10.2 g (82.6 mmol) of R-3-hydroxypyrrolidine hydrochloride (Chem. Letts., 1966, pp 893–6) in 50 m of water was cooled to 0° and treated with 22.5 ml (90 mmol) of 4.0 N sodium hydroxide. The neutral solution was treated dropwise with 15.6 g (87 mmol) of carbobenzyloxy chloride maintaining the pH at 11.0±0.5 by the dropwise addition of 87 ml of 1.0 N sodium hydroxide and the temperature below 5° with a salt-ice bath. When the addition was complete, the mixture was stirred at 5° for two hours and stored at 5° for 18 hours. The reaction mixture was saturated with sodium chloride and extracted with ethyl acetate (2 ×500 ml). The combined organic layers were washed with 1.0 N sodium hydroxide (4×50 ml), water, dried (MgSO$_4$) and evaporated in vacuo to give 17.5 g of the title compound.

(S)-3-Hydroxy-1-pyrrolidinecarboxylic acid, phenylmethyl ester

When the above procedure was repeated using 12.4 g (0.1 mol) of (S)-3-hydroxypyrrolidine hydrochloride, the yield of the title compound was 20.1 g.

(R)-3-(Methylsulfonyl)oxy]-1-pyrrolidinecarboxylic acid, phenylmethyl ester

A solution of 17.5 g (84 mmol) of (R)-3-hydroxy-1-pyrrolidinecarboxylic acid, phenylmethyl ester in 150 ml of dry pyridine was cooled to 5° and treated dropwise with 11.5 g (0.1 mol) of methanesulfonyl chloride keeping the temperature at 5°. The reaction mixture was stirred at 5° for two hours and stored at 5° for 18 hours. The reaction mixture was allowed to warm to room temperature over three hours and the solvent was then removed in vacuo. The residue was partitioned between ethyl acetate/water (500 ml each) and the aqueous layer was reextracted with ethyl acetate. The combined organic layers were washed with water, dried (MgSO$_4$), and evaporated in vacuo to give 21.2 g of the title compound.

(S)-3-[(Methylsulfonyl)oxy]-1-pyrrolidinecarboxylic acid, phenylmethyl ester When the above reaction was run using 19.7 g (89 mmol) of the (S)-isomer, the yield of the title compound was 26.2 g.

(S)-3-Azido-1-pyrrolidinecarboxylic acid, phenylmethyl ester

A solution of 20.5 g (72 mmol) of (R)-3-[(methylsulfonyl)oxy]-1-pyrrolidinecarboxylic acid, phenylmethyl ester in 100 ml of dry N,N-dimethylformamide was treated with 6.5 g (0.1 mol) of sodium azide and heated at 90° for four hours. The solvent was removed in high vacuo at 50° and the residue was partitioned between ethyl acetate/water (250 ml each). The aqueous layer was reextracted with ethyl acetate and the combined organic fractions were washed with water, dried (MgSO$_4$) and evaporated in vacuo to give 16.2 g of the title compound.

(R)-3-Azido-1-pyrrolidinecarboxylic acid, phenylmethyl ester

When the above reaction was run using 21.0 g (70 mmol) of the S-isomer, the yield of the title compound was 15.2 g.

(S)-3-Amino-1-pyrrolidinecarboxylic acid, phenylmethyl ester

A solution of 14.7 g (60 mmol) of (S)-3-azido-1-pyrrolidinecarboxylic acid, phenylmethyl ester in 200 ml of methanol was treated with 1.0 g of Raney-nickel and shaken in a hydrogen atmosphere at pressures of 49.5–51 psi and temperatures of 25.3–29.5° for nine hours. The catalyst was removed by filtration and the solvent was removed in vacuo to give 13.2 g of the title compound.

(R)-3-Amino-1-pyrrolidinecarboxylic acid, phenylmethyl ester

When the above reaction was run using 15.1 g (61 mmol) of the (R)-isomer, the yield of the title compound was 13.4 g.

(S)-3-[[(1,1-Dimethylethoxy)carbonyl]amino]-1-pyrrolidinecarboxylic acid, phenylmethyl ester To a solution of 13.7 g (60 mmol) of(S-3-amino-1-pyrrolidinecarboxylic acid, phenylmethyl ester in a mixture of 59 ml of 1.0 N sodium hydroxide and 90 ml of t-butanol was added dropwise a solution of 13.1 g (60 mmol) of di-tert-butyl dicarbonate in 20 ml of t-butanol keeping the temperature below 40°. The reaction was allowed to come to room temperature over 18 hours and the t-butanol was evaporated in vacuo. The residue was partitioned between ethyl acetate/water (250 ml of each) and the aqueous layer was reextracted with ethyl acetate (250 ml). The combined ethyl acetate layers were washed with water, dried (MgSO<), filtered, and evaporated in vacuo to give 18.2 g of the title compound, mp 124°–125°.

(R)-3-[[(1,1-Dimethylethoxy)carbonyl]amino]-1-pyrrolidinecarboxylic acid, phenylmethyl ester When the above reaction was run using 17.6 g (80 mmol) of (R)-3-amino-1-pyrrolidinecarboxylic acid, phenylmethyl ester, the yield of the title compound was 24.8 g.

(S)-3-[[(1,1-Dimethylethoxy)carbonyl]amino]pyrrolidine

A solution of 17.7 g (55.2 mmol) of (S)-3-[[(1,1-dimethylethoxy)carbonyl]amino]-1-pyrrolidinecarboxylic acid, phenylmethyl ester, in 400 ml of methanol was treated with 2.0 g of 20% palladium on carbon and shaken in an atmosphere of hydrogen at temperatures of 22°–26.5° and pressures of 45–50.5 psi for one hour. The solvent was removed in vacuo to give 10.1 g of the title compound.

(R)-3-[[(1,1-Dimethylethoxy)carbonyl]amino]pyrrolidine

When the above reaction was run using 22.4 g (70 mmol) of (R)-3-[[(1,1-dimethylethoxy)carbonyl]amino]-1-pyrrolidinecarboxylic acid, phenylmethyl ester, the yield of the title compound was 12.5 g.

EXAMPLE 1

(S)-1-Cyclopropyl-7-[3-[[(1,1-dimethylethoxy)carbonyl]-amino]-1-pyrrolidinyl]-6-fluoro-1,4-dihydro-4-oxo-1,8- naphthyridine-3-carboxylic acid A suspension of 1.13 g (4.0 mmol) of 7-chloro-1-cyclopropyl-6-fluoro-1,4-dihydro-4-oxo-1,8-naphthyridine-3-carboxylic acid, 1.3 g (7.0 mmol) of (S)-3-[[(1,1-dimethylethoxy)carbonyl$\pi$amino]pyrrolidine, 1.2 g (12 mmol) of triethylamine and 50 ml of acetonitrile was stirred at room temperature for 24 hours. The mixture was cooled to 5°, the solid was removed by filtration, washed with acetonitrile, ether, and dried in vacuo to give 1.5 g of the title compound, mp 247°–249°, which was used for the next step without further purification.

EXAMPLE 2

(R)-1-Cyclopropyl-7-[3-[[(1,1-dimethylethoxy)carbonyl]-amino]-1-pyrrolidinyl]-6-fluoro-1,4-dihydro-4-oxo-1,8-naphthyridine-3-carboxylic acid When the above reaction was run using 1.3 g (7.0 mmol) of (R)-3-[[(1,1-dimethylethoxy)carbonyl]amino]pyrrolidine, the yield of the title compound was 1.4 g (85%).

EXAMPLE 3

(S)-7-(3-Amino-1-pyrrolidinyl)-1-cyclopropyl-6-fluoro-1,4-dihydro-4-oxo-1,8-naphthyridine-3-carboxylic acid A suspension of 1.5 g (3.6 mmol) of (S)-1-cyclopropyl-7-[3-(1,1-dimethylethoxy)carbonyl]-amino]-1-pyrrolidinyl]-6-fluoro-1,4-dihydro-4-oxo1,8-naphthyridine-3-carboxylic acid in a solution of 25 ml of 1.0 M hydrochloric acid and 25 ml of ethanol was stirred at room temperature for one-half hour and then heated to 60° for one-half hour. The resulting solution was cooled to room temperature, filtered through a fiber glass pad to clarify, and the filtrate was evaporated. The residue was triturated with 2-propanol (25 ml), diluted with ether (25 ml), and the solid was removed by filtration. After washing with 2-propanol/ether (2×10 ml of 1:1) ether and drying in vacuo, the yield of the title compound was 1.18 g and melted 296°–298°.

EXAMPLE 4

(R)-7-(3-Amino-1-pyrrolidinyl)-1-cyclopropyl-6-fluoro-1,4-dihydro-4-oxo-1,8-naphthyridine-3carboxylic acid hydrochloride When the above procedure was carried out using 1.4 g (3.4 mmol) of (R)-1-cyclopropyl-7-[3-[[(1,1-dimethylethoxy)carbonyl]amino]-1-pyrrolidinyl]-6-fluoro-1,4-dihydro-4-oxo-1,8-naphthyridine-3-carboxylic acid, the yield of the title compound was 1.1 g and melted 297°–299°.

I claim:

1. Substantially pure (S)-7-(3-amino-1-pyrrolidinyl)-1-cyclopropyl-6- fluoro-1,4-dihydro-4-oxo-1,8-naphthyridine-3-carboxylic acid, a lower alkyl ester or a pharmaceutically acceptable acid addition or base salt thereof.

2. A compound as claimed in claim 1 and being (S)-7-(3-amino-1-pyrrolidinyl)-1-cyclopropyl-6- fluoro-1,4-dihydro-4-oxo-1,8-naphthyridine-3-carboxylic acid.

3. A pharmaceutical composition comprising an antibacterially effective amount of a compound as claimed in claim 1 together with a pharmaceutically acceptable carrier.

4. The method of treating bacterial infections in mammals which comprises administering to said mammal in need thereof a pharmaceutical composition as claimed in claim 3.

* * * * *